U S 010863892B2

(12) United States Patent
Saito

(10) Patent No.: US 10,863,892 B2
(45) Date of Patent: Dec. 15, 2020

(54) IMAGING DEVICE AND ENDOSCOPE SYSTEM

(71) Applicant: OLYMPUS CORPORATION, Tokyo (JP)

(72) Inventor: Kanako Saito, Mitaka (JP)

(73) Assignee: OLYMPUS CORPORATION, Tokyo (JP)

( * ) Notice: Subject to any disclaimer, the term of this patent is extended or adjusted under 35 U.S.C. 154(b) by 385 days.

(21) Appl. No.: 15/956,962

(22) Filed: Apr. 19, 2018

(65) Prior Publication Data
US 2018/0235450 A1 Aug. 23, 2018

Related U.S. Application Data

(63) Continuation of application No. PCT/JP2015/080619, filed on Oct. 29, 2015.

(51) Int. Cl.
| | | |
|---|---|---|
| A61B 1/045 | (2006.01) | |
| A61B 1/05 | (2006.01) | |
| A61B 1/00 | (2006.01) | |

(52) U.S. Cl.
CPC .......... *A61B 1/045* (2013.01); *A61B 1/00006* (2013.01); *A61B 1/00009* (2013.01);
(Continued)

(58) Field of Classification Search
CPC . A61B 1/045; A61B 1/00006; A61B 1/00096; A61B 1/00133; A61B 1/00188
See application file for complete search history.

(56) References Cited

U.S. PATENT DOCUMENTS

| | | | |
|---|---|---|---|
| 6,271,883 B1 | 8/2001 | Iijima et al. | |
| 6,512,549 B1 * | 1/2003 | Iijima | ................ H04N 5/23212 348/349 |

(Continued)

FOREIGN PATENT DOCUMENTS

| | | |
|---|---|---|
| CN | 1956501 A | 5/2007 |
| CN | 202602794 A | 12/2012 |

(Continued)

OTHER PUBLICATIONS

Chinese Search Report dated Dec. 16, 2019 in Chinese Patent Application No. 201580084026.1, together with English machine translation.

(Continued)

*Primary Examiner* — Timothy J Neal
*Assistant Examiner* — Jae Woo
(74) *Attorney, Agent, or Firm* — Scully, Scott, Murphy & Presser, P.C.

(57) ABSTRACT

An imaging device includes: an optical device; a movable frame configured to support and move the optical device in a predetermined direction; a supporting frame configured to support the movable frame; a voice coil motor configured to move the movable frame relative to the supporting frame in the predetermined direction; a position detecting unit configured to detect a position of the movable frame relative to the supporting frame and generate a position signal; a signal processing unit configured to generate a drive signal and determine whether the position signal is normal; an imaging device; an image processing unit; a first drive controller configured to drive the movable frame; a second drive controller configured to drive the movable frame; and a selector configured to select a drive controller that controls driving of the movable frame from the first drive controller and the second drive controller.

17 Claims, 6 Drawing Sheets

(52) U.S. Cl.
CPC ...... *A61B 1/00096* (2013.01); *A61B 1/00133* (2013.01); *A61B 1/00188* (2013.01); *A61B 1/05* (2013.01)

(56) References Cited

U.S. PATENT DOCUMENTS

| | | | |
|---|---|---|---|
| 9,122,129 B2 | 9/2015 | Hamamura | |
| 9,516,999 B2* | 12/2016 | Higuchi | G02B 7/34 |
| 2007/0086767 A1 | 4/2007 | Nakai | |
| 2007/0127904 A1* | 6/2007 | Iwasaki | G02B 7/102 |
| | | | 396/55 |
| 2007/0206937 A1 | 9/2007 | Kusaka | |
| 2012/0150471 A1 | 6/2012 | Muto | |
| 2012/0268642 A1* | 10/2012 | Kawai | G02B 27/646 |
| | | | 348/335 |
| 2013/0321938 A1* | 12/2013 | Ohno | G02B 7/09 |
| | | | 359/824 |
| 2014/0039257 A1* | 2/2014 | Higuchi | A61B 1/00006 |
| | | | 600/109 |
| 2016/0037079 A1* | 2/2016 | Gocho | G02B 23/2438 |
| | | | 348/240.3 |
| 2016/0282601 A1* | 9/2016 | Kono | A61B 1/00188 |
| 2018/0052298 A1* | 2/2018 | Sueoka | G02B 7/08 |
| 2018/0205862 A1* | 7/2018 | Ishikawa | H04N 5/2253 |
| 2019/0238753 A1* | 8/2019 | Urakami | H04N 5/23258 |
| 2020/0166740 A1* | 5/2020 | Nagamizu | A61B 1/00096 |

FOREIGN PATENT DOCUMENTS

| | | |
|---|---|---|
| JP | H04-331907 A | 11/1992 |
| JP | H05-053044 A | 3/1993 |
| JP | H06-205265 A | 7/1994 |
| JP | 2007-233032 A | 9/2007 |
| JP | 2011-138007 A | 7/2011 |
| JP | 2013-109107 A | 6/2013 |
| JP | 2013-130643 A | 7/2013 |
| JP | 5384320 B2 | 1/2014 |
| WO | WO 2015/015877 A1 | 2/2015 |

OTHER PUBLICATIONS

Chinese Office Action dated Jun. 3, 2019 issued in Chinese Patent Application No. 201580084026.1.
International Search Report dated Jan. 26, 2016 issued in PCT/JP2015/080619.

* cited by examiner

IMAGING DEVICE AND ENDOSCOPE SYSTEM

CROSS-REFERENCE TO RELATED APPLICATION

This application is a continuation of International Application No. PCT/JP2015/080619, filed on Oct. 29, 2015, the entire contents of which are incorporated herein by reference.

BACKGROUND

The present disclosure relates to an imaging device and an endoscope system.

In widely used endoscope systems, an endoscope is introduced into a living body, and an image of the subject captured by the endoscope is observed to diagnose the living body. In the endoscope systems, the depth of field needs to be as large as possible so as not to obstruct diagnosis and treatment by technicians such as doctors or nurses. In recent years, the depth of field has been smaller due to an increase in the number of pixels of imaging devices, and therefore there is a disclosure of endoscope systems in which automatic focus (hereafter, referred to as auto focus (AF)) is conducted to focus on objects. Typically, voice coil motors (VCM) are often used as actuators for conducting auto focus.

A problem peculiar to endoscopes is that even if a drive unit for conducting AF during treatment is out of control, there is a need to keep such a resolution that the treatment may be continued without removing an endoscope from the subject. For example, position detection devices that detect the position of a movable lens are electrically sensitive and they are likely to be damaged due to temperature, humidity, and the like; therefore, there is a need to take measures for failures of the position detection devices. As the technology for taking the measures, there is a disclosure of the technology in which an absolute-position detection sensor that detects the absolute value of the position of a movable lens and a relative-position detection sensor that detects the amount of displacement of a movable lens are provided, it is detected whether the relative-position detection sensor is faulty by using a detection result of each sensor, and the position of the movable lens is determined in accordance with a detection result of the absolute-position detection sensor if the relative-position detection sensor is faulty (for example, see Japanese Patent No. 5384320).

SUMMARY

An imaging device according to one aspect of the present disclosure includes: an optical device configured to transmit light; a movable frame configured to support and move the optical device in a predetermined direction; a supporting frame configured to support the movable frame; a voice coil motor including a magnet and a coil and configured to move the movable frame relative to the supporting frame in the predetermined direction; a position detecting unit configured to detect information about a position of the movable frame relative to the supporting frame and generate a position signal; a signal processing unit configured to generate a drive signal including information about a movement distance and a moving direction of the movable frame relative to the supporting frame in accordance with the position signal generated by the position detecting unit and determine whether the position signal is normal; an imaging device configured to conduct photoelectric conversion on light passed through the optical device to generate an imaging signal; an image processing unit configured to generate an image signal based on the imaging signal; a first drive controller configured to drive the movable frame by controlling a current flowing through the coil in accordance with the drive signal generated by the signal processing unit; a second drive controller configured to drive the movable frame by controlling a current flowing through the coil in accordance with the image signal generated by the image processing unit; and a selector configured to select a drive controller that controls driving of the movable frame from the first drive controller and the second drive controller in accordance with a determination result of the signal processing unit.

The above and other features, advantages and technical and industrial significance of this disclosure will be better understood by reading the following detailed description of presently preferred embodiments of the disclosure, when considered in connection with the accompanying drawings.

DETAILED DESCRIPTION

Embodiments for implementing the present disclosure are explained below.

First Embodiment

Figure 1:
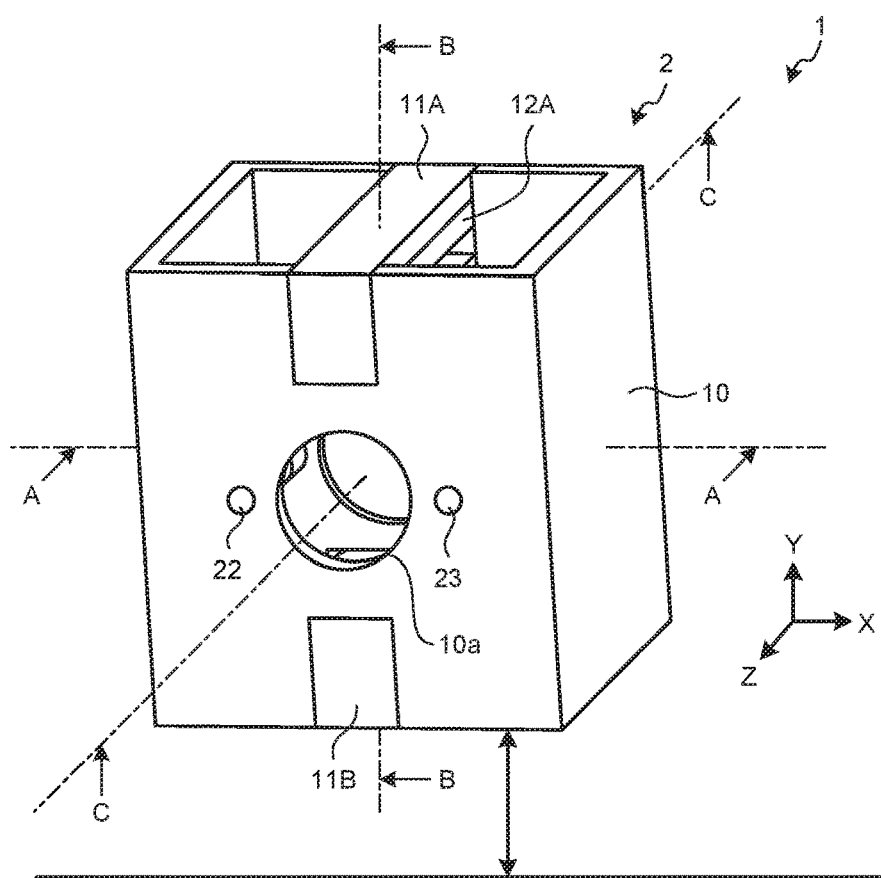
FIG. 1 is a schematic diagram that illustrates a schematic configuration of an optical system according to a first embodiment.
Figure 1:
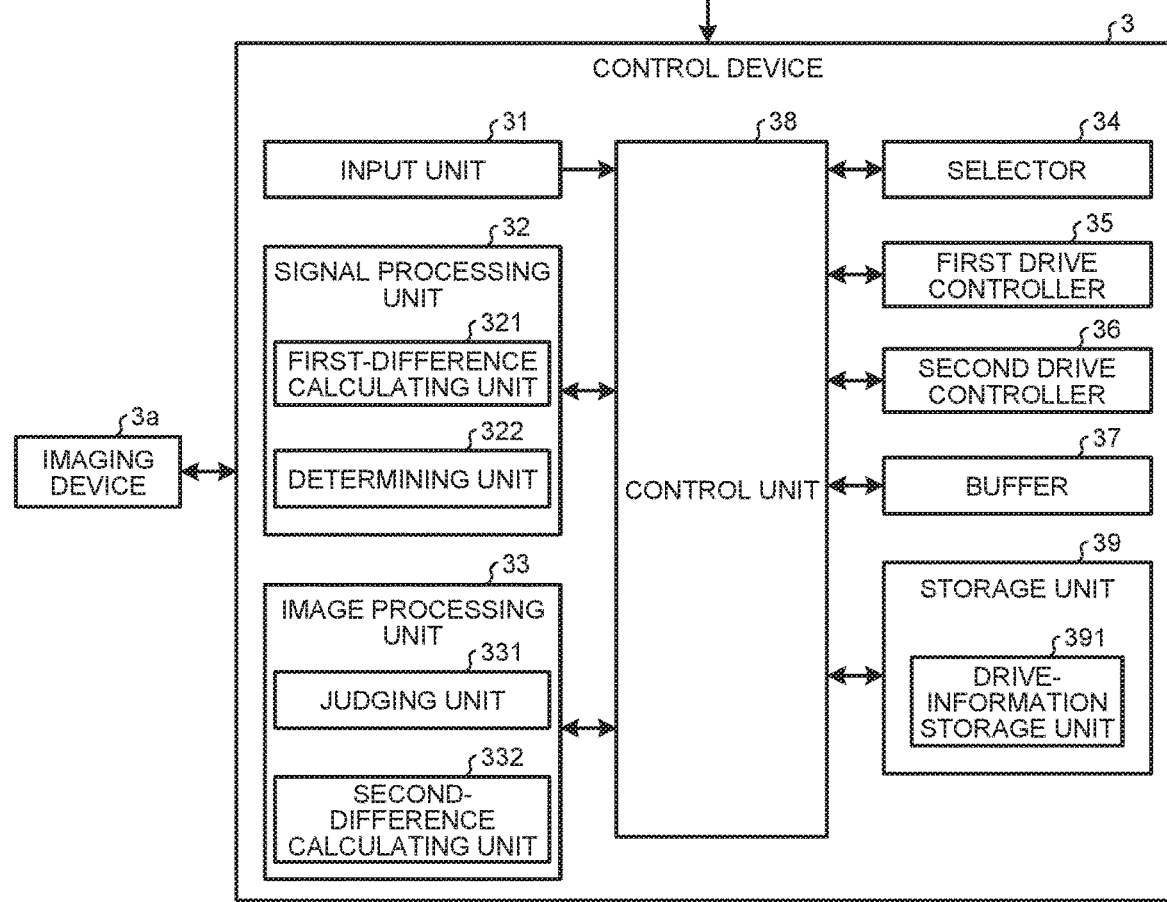
Figure 2:
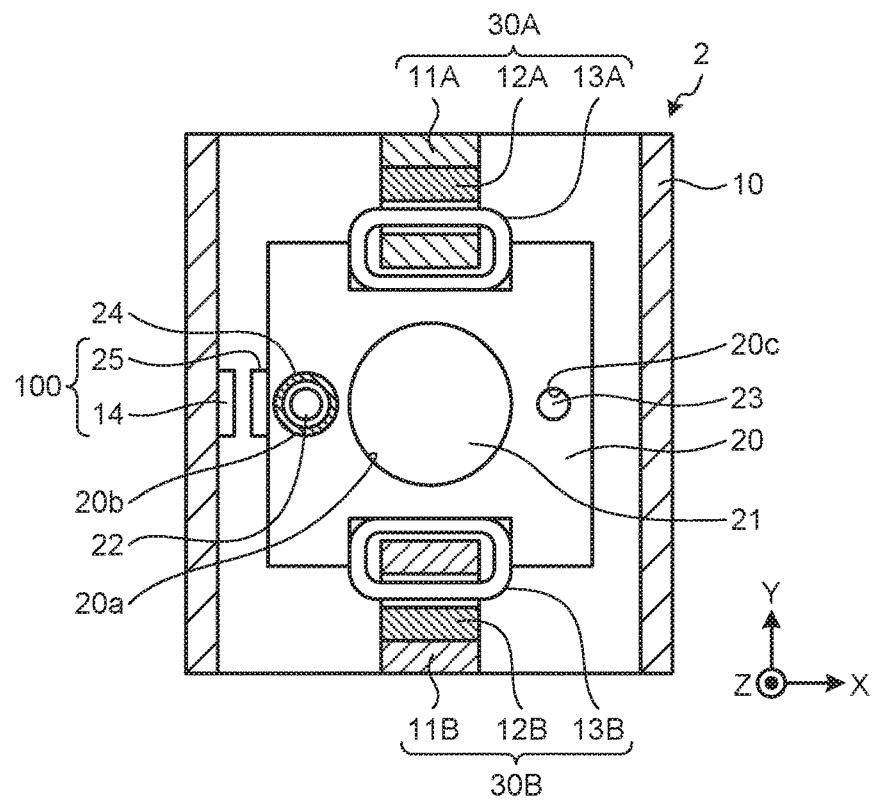
FIG. 2 is a cross-sectional view taken along the line A-A of FIG. 1.
Figure 3:
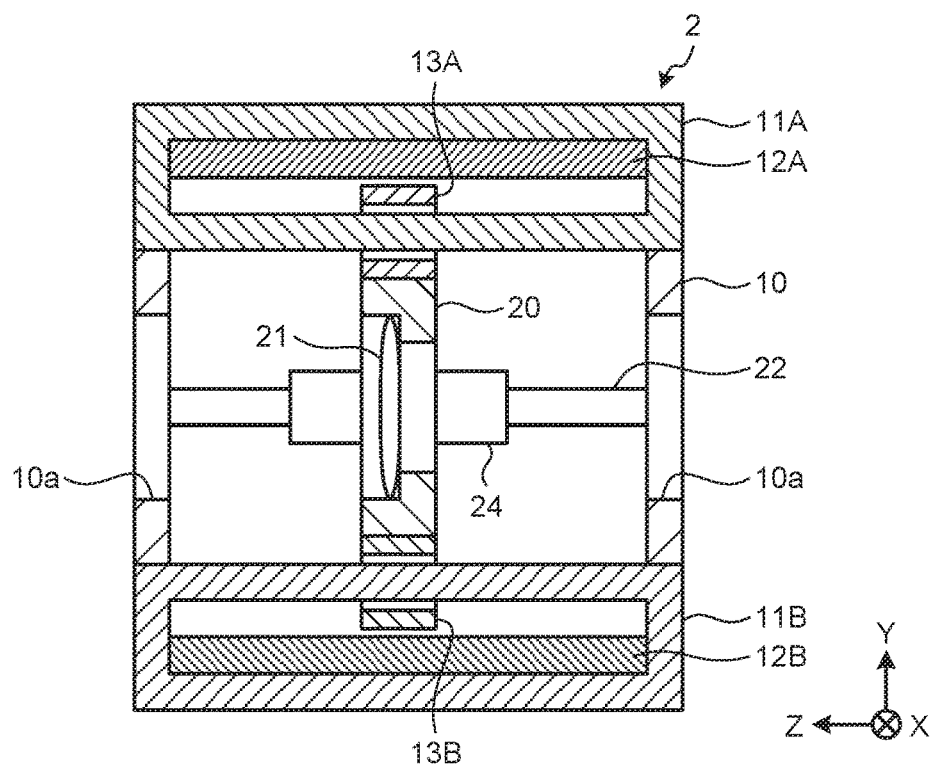
FIG. 3 is a cross-sectional view taken along the line B-B of FIG. 1.
Figure 4:
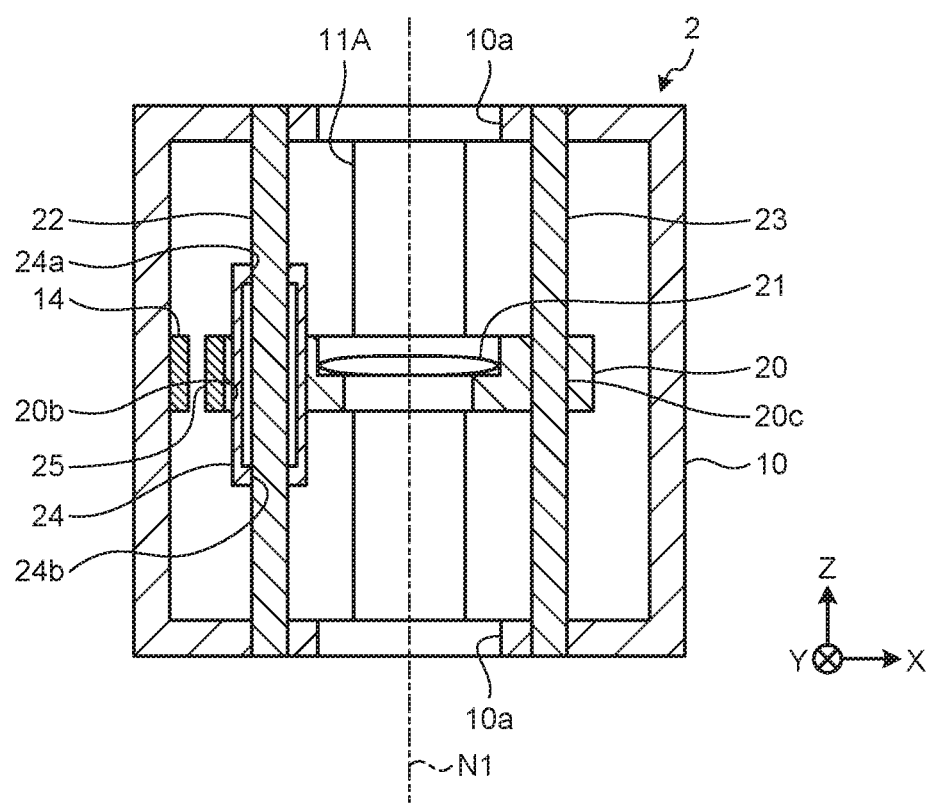
FIG. 4 is a cross-sectional view taken along the line C-C of FIG. 1.

FIG. 1 is a schematic diagram that illustrates a schematic configuration of an optical system according to a first embodiment. FIG. 2 is a cross-sectional view taken along the line A-A of FIG. 1 and, the plane parallel to the XY plane in the Cartesian coordinate system illustrated in FIG. 1 is a cut plane in the cross-sectional view. FIG. 3 is a cross-sectional view taken along the line B-B of FIG. 1, and the plane parallel to the YZ plane in the Cartesian coordinate system illustrated in FIG. 1 is a cut plane in the cross-sectional view. FIG. 4 is a cross-sectional view taken along the line C-C of FIG. 1, and the plane parallel to the XZ plane in the Cartesian coordinate system illustrated in FIG. 1 is a cut plane in the cross-sectional view. With regard to the cross-sectional views illustrated in FIGS. 2 to 4, an explanation is given based on the assumption that the cut plane passes through the center of a movable lens 21 described later.

An optical system 1 illustrated in FIG. 1 includes an optical unit 2 that is capable of moving a lens in the direction of a light axis; a control device 3 that controls driving of each component including the optical unit 2 and controls input/output of information to and from each component; and an imaging device 3a that performs a photoelectric conversion process on light received via the optical unit 2.

The imaging device 3a is implemented by using an imaging device where pixels are arranged in two dimensions to generate imaging signals by receiving light and conducting photoelectric conversion. Imaging devices include, for example, CCD (charge coupled device) image sensors or CMOS (complementary metal oxide semiconductor) image sensors. The imaging device 3a has a light receiving surface provided at a position that is parallel to the XY plane and is perpendicular to the optical axis of the optical unit 2, and it outputs generated imaging signals to the control device 3.

The optical unit 2 includes a fixed frame 10 (supporting frame) that is fixed to a casing of the imaging device or the distal end of the endoscope; a movable frame 20 that is movable relative to the fixed frame 10; the movable lens 21 that is provided in the movable frame 20; a primary shaft 22 that supports the movable frame 20 and guides the moving direction of the movable frame 20 relative to the fixed frame 10; a secondary shaft 23 that supports the movable frame 20 and guides the moving direction of the movable frame 20 relative to the fixed frame 10; a shaft bearing 24 that is fixed to the movable frame 20 and is in contact with the primary shaft 22 in a slidable manner; voice coil motors 30A, 30B that generate driving force for moving the movable frame 20 relative to the fixed frame 10; and a position detecting unit 100 that detects the position of the movable frame 20 relative to the fixed frame 10.

The fixed frame 10 is shaped like a rectangular hollow column where a prismatic hollow space is formed. In the fixed frame 10, a through-hole 10a is formed which passes through in a direction (the Z-axis direction illustrated in FIG. 1 according to the first embodiment) perpendicular to the central axis of the rectangular hollow column in a penetrating direction. Furthermore, a yoke 11A described later is provided at one end with respect to an aperture direction (the Y-axis direction illustrated in FIG. 1 according to the first embodiment) of the fixed frame 10, and a yoke 11B described later is provided at the other end with respect to the aperture direction. The yokes 11A, 11B are ring-shaped by being formed by using material such as iron with high magnetic permeability.

The movable frame 20 is provided with a supporting hole 20a that supports the movable lens 21; an insertion hole 20b that supports the inserted shaft bearing 24; and an insertion hole 20c that supports the inserted secondary shaft 23. The movable frame 20 supports the movable lens 21 such that the movable lens 21's optical axis extending in the Z-axis direction, e.g., an axis N1 illustrated in FIG. 4, substantially matches the central axis of the through-hole 10a. The insertion hole 20b is a hole that has a diameter that corresponds to the outer diameter of the shaft bearing 24. The insertion hole 20c is a hole that has a diameter that corresponds to the outer diameter of the secondary shaft 23. It is preferable that the movable frame 20 is formed by using light metal or high-temperature resin in terms of heat resistance. Light metals include metals such as aluminum, magnesium, titanium, or beryllium, alloy including these metals, and the like. High-temperature resin includes for example resin that has heat resistance for over 60° C. The movable lens 21 is formed by using one or more lenses.

The primary shaft 22 extends like a rod in the Z-axis direction, and both ends thereof are fixed to the fixed frame 10. It is preferable that the primary shaft 22 is formed by using metallic material or alloy in terms of heat resistance.

The secondary shaft 23 extends like a rod in the Z-axis direction, and both ends thereof are fixed to the fixed frame 10. The secondary shaft 23 is provided at the opposite side of the primary shaft 22 with respect to the central axis of the movable lens 21. It is preferable that the secondary shaft 23 is formed by using metallic material or alloy in terms of heat resistance.

The shaft bearing 24 is shaped like a cylinder that extends in the Z-axis direction, it covers part of the outer circumference of the primary shaft 22, and it is supported by the movable frame 20. The shaft bearing 24 includes slide portions 24a, 24b that are provided at two ends and that are in contact with the primary shaft 22 in a slidable manner. It is preferable that the shaft bearing 24 is formed by using metallic material, alloy, or high-temperature resin in terms of heat resistance.

Lubricant agent is applied to the outer circumference of the primary shaft 22 or the portions (ends) of the shaft bearing 24 that is in contact with the primary shaft 22. The lubricant agent includes grease, lubricant oil, and the like. Furthermore, a solid lubricant may be provided as a lubricant means, or coating processing may be performed by fluorine lubrication plating, lubrication alumite, or the like. It is preferable that the lubricant means has a heat resistance property under high temperature, e.g., over 60° C., and the above-described means is not a limitation as long as lubrication effect may be achieved.

The voice coil motor 30A includes the yoke 11A, a magnet 12A that is attached to the inner circumference of the yoke 11A, and a coil 13A that is supported by the movable frame 20 and that is wound around the yoke 11A at the opposite of the side where the magnet 12A is attached. The magnet 12A is implemented by using a permanent magnet, and it has a shape extending in the Z-axis direction.

The voice coil motor 30B includes the yoke 11B, a magnet 12B that is attached to the inner circumference of the yoke 11B, and a coil 13B that is supported by the movable frame 20 and that is wound around the yoke 11B at the opposite of the side where the magnet 12B is attached. The magnet 12B is implemented by using a permanent magnet, and it has a shape extending in the Z-axis direction.

In this case, the magnetic polarization direction of the magnets 12A, 12B is the Y-axis direction perpendicular to the light-axis direction (the Z-axis direction) of the movable lens 21. Furthermore, more generally, the magnetic polarization direction of the magnets 12A, 12B may be any direction that intersects with the optical-axis (Z-axis) direction.

When currents flow into the coils 13A, 13B, a force in the Z-axis direction occurs in the movable frame 20 due to an effect of the magnetic fields of the magnets 12A, 12B so that the movable frame 20 moves in the Z-axis direction relative to the fixed frame 10. For example, by controlling the current flowing in each of the coils 13A, 13B, the movable frame 20 may be moved in a desired direction along the primary shaft 22.

The position detecting unit 100 includes a single Hall element 14 that is a position detection sensor attached to the fixed frame 10 and a detection magnet 25 provided in the movable frame 20. The Hall element 14 detects the intensity of a magnetic field at a predetermined time interval, sequentially converts the detected intensity of the magnetic field into a voltage value, and outputs it as a position signal to the control device 3. The Hall element 14 detects, for example, a magnetic field in a direction perpendicular to the longitudinal direction of the primary shaft 22 (the moving direction of the movable frame 20). The detection magnet 25 is provided near the primary shaft 22 on a side surface in the direction perpendicular to the optical axis of the movable frame 20. Furthermore, it is preferable that the detection magnet 25 is provided at the position where the straight line passing through its center and extending in the X-axis direction intersects with the central axes of the primary shaft 22 and the secondary shaft 23.

Next, a configuration of the control device 3 is explained. The control device 3 includes an input unit 31, a signal processing unit 32, an image processing unit 33, a selector 34, a first drive controller 35, a second drive controller 36, a buffer 37, a control unit 38, and a storage unit 39. Furthermore, an imaging device is configured by using the fixed frame 10, the movable frame 20, the movable lens 21, the voice coil motors 30A, 30B, the position detecting unit 100, the signal processing unit 32, the image processing unit 33, the selector 34, the first drive controller 35, and the second drive controller 36.

The input unit 31 is an interface for making input from users to the control device 3, and the like, and it includes a power switch for turning on/off the power source, a command input button for instructing the target position or the moving direction of the movable frame 20, or the like. Furthermore, command signals (command values) for focusing (movement of the movable frame 20) are input via the input unit 31 if a focusing operation is manually performed, and a focusing operation is performed under the control of the control unit 38 if automatic focusing is performed. Command values include numerical values that indicate the position of the movable frame 20, e.g., numerical values that are assigned in a moveable range of the movable frame 20 and that indicate a position in the movable range.

The signal processing unit 32 calculates the difference between the current position of the movable frame 20 and the position designated by a command input that is input via the input unit 31 for manual focusing or a command input that is input from the control unit 38 for automatic focusing so as to determine the movement distance and the moving direction of the movable frame 20 and, on the basis of the difference, determines whether the position signal acquired by the position detecting unit 100 is faulty. The signal processing unit 32 includes a first-difference calculating unit 321 and a determining unit 322.

The first-difference calculating unit 321 calculates the difference between the current position of the movable frame 20 and the above-described position designated by a command input. The difference is a value that indicates the movement distance and the moving direction of the movable frame 20. The moving direction is obtained by determining whether it is one direction (e.g., + direction) or the other direction (e.g., − direction) with respect to a predetermined direction on the basis of whether the difference between the current position (signal value) of the movable frame 20 and the position (command value) designated by a command input is positive or negative. The first-difference calculating unit 321 inputs the calculated difference to the buffer 37.

The determining unit 322 determines whether the position signal acquired by the position detecting unit 100 is faulty on the basis of the difference calculated by the first-difference calculating unit 321. For example, the determining unit 322 compares the obtained difference with the previous difference acquired from the buffer 37 while the movable frame 20 is in the middle of drive control and determines that it is faulty when the difference hardly changes while the movable frame 20 is moving and the difference is equal to or more than a threshold so that the target position is not reached. The determining unit 322 inputs a determination result to the image processing unit 33 and, if the position signal is not faulty, inputs the difference as a drive signal to the first drive controller 35. Furthermore, a threshold is provided to determine whether a movement is being made, and the determining unit 322 determines that a movement is being made when the difference calculated by the first-difference calculating unit 321 is equal to or more than the threshold.

The image processing unit 33 uses imaging signals generated by the imaging device 3a to generate image data displayed by an external display device. The image processing unit 33 performs predetermined image processing on imaging signals to generate image data including capturing images. Capturing images are color images that each has R, G, and B values that are variables when an RGB color system is used as a color space. The image processing unit 33 inputs image data that includes contrast values of capturing images to the buffer 37. The contrast values mentioned here are the ratio between the luminance value of the brightest area in a capturing image and the luminance value of the darkest area.

Furthermore, the image processing unit 33 includes a judging unit 331 and a second-difference calculating unit 332. The judging unit 331 acquires a determination result of the determining unit 322 and determines whether a position signal is faulty on the basis of the determination result. If the judging unit 331 determines that the position signal is faulty, the second-difference calculating unit 332 acquires a contrast value (representative signal value) in the image data immediately before the latest image data from the buffer 37 and calculates the difference between the contrast value (representative signal value) in the latest image data and the contrast value in the previous image data. In the same manner as the above-described difference calculated by the first-difference calculating unit 321, the value and the positive/negative of the difference indicate the movement distance and the moving direction of the movable frame 20 where the direction in which a contrast value increases is positive. The second-difference calculating unit 332 inputs the calculated difference to the buffer 37 and inputs the difference as a drive signal to the second drive controller 36.

The selector 34 acquires a determination result of the determining unit 322 and, in accordance with a determination result, changes (sets) a drive controller between the first drive controller 35 and the second drive controller 36 to control driving of the movable frame 20. If a determination result of the determining unit 322 indicates that the position signal is not faulty, the selector 34 sets the first drive controller 35 as a drive controller for controlling driving. Conversely, if a determination result of the determining unit 322 indicates that the position signal is faulty, the selector 34 sets the second drive controller 36 as a drive controller for controlling driving.

The first drive controller 35 controls driving of the movable frame 20 by controlling currents so as to flow into the coils 13A, 13B to keep the stop position of the movable frame 20 or by controlling currents so as to flow into the coils 13A, 13B to move the movable frame 20 in accordance with the difference calculated by the first-difference calculating unit 321. The first drive controller 35 acquires a drive signal that is a difference from the first-difference calculating unit 321 and then adjusts for example the amplitude or phase of the drive signal. The first drive controller 35 causes currents to flow into the coils 13A, 13B via the control unit 38 with the current value that corresponds to the adjusted drive signal, thereby controlling driving of the movable frame 20.

The second drive controller 36 controls driving of the movable frame 20 by controlling currents so as to flow into the coils 13A, 13B to keep the stop position of the movable frame 20 or by controlling currents so as to flow into the coils 13A, 13B to move the movable frame 20 in accordance with the difference calculated by the second-difference calculating unit 332. The second drive controller 36 acquires a drive signal that is a difference from the second-difference calculating unit 332 and then adjusts for example the amplitude or phase of the drive signal. The second drive controller 36 causes currents to flow into the coils 13A, 13B via the control unit 38 with the current value that corresponds to the adjusted drive signal, thereby controlling driving of the movable frame 20. According to the first embodiment, on the basis of a difference, the second drive controller 36 performs control so as to move the movable frame 20 to the position that obtains the contrast value in the image data immediately before it is determined that a position signal is faulty. Furthermore, for gain adjustment conducted by the first drive controller 35 and gain adjustment conducted by the second drive controller 36, the value of a drive signal input to each of the drive controllers is different, and therefore the amplification factor of drive signals are different.

The buffer 37 is implemented by using for example a ring buffer, and it stores differences calculated by the first-difference calculating unit 321 and image data (including contrast values) generated by the image processing unit 33 in chronological order. If it runs out of space, the earliest information is written over with the latest information so that the latest information is stored in chronological order.

The control unit 38 is configured by using a CPU (central processing unit), or the like, and it controls driving of each component including the optical unit 2, controls input/output of information to/from each component, and the like. The control unit 38 transmits signals (currents that correspond to current values), or the like, generated by the first drive controller 35 or the second drive controller 36 to the optical unit 2 via a predetermined signal line. For automatic focusing, the control unit 38 generates command values for designating a move position of the movable frame 20 on the basis of image signals and performs control on the movable frame 20.

The storage unit 39 stores various programs for operating the optical system 1 and data that includes various parameters needed for operation of the optical system 1. The storage unit 39 is implemented by using a semiconductor memory such as a flash memory or a DRAM (dynamic random access memory). Furthermore, the storage unit 39 includes a drive-information storage unit 391 that stores a reference value for the amount of change in a difference, which is a threshold for determining whether a position signal is faulty, a threshold for determining whether a target position is reached (a fixed position is being kept), a threshold for determining whether the movable frame 20 is being moved, or the like.

Figure 5:
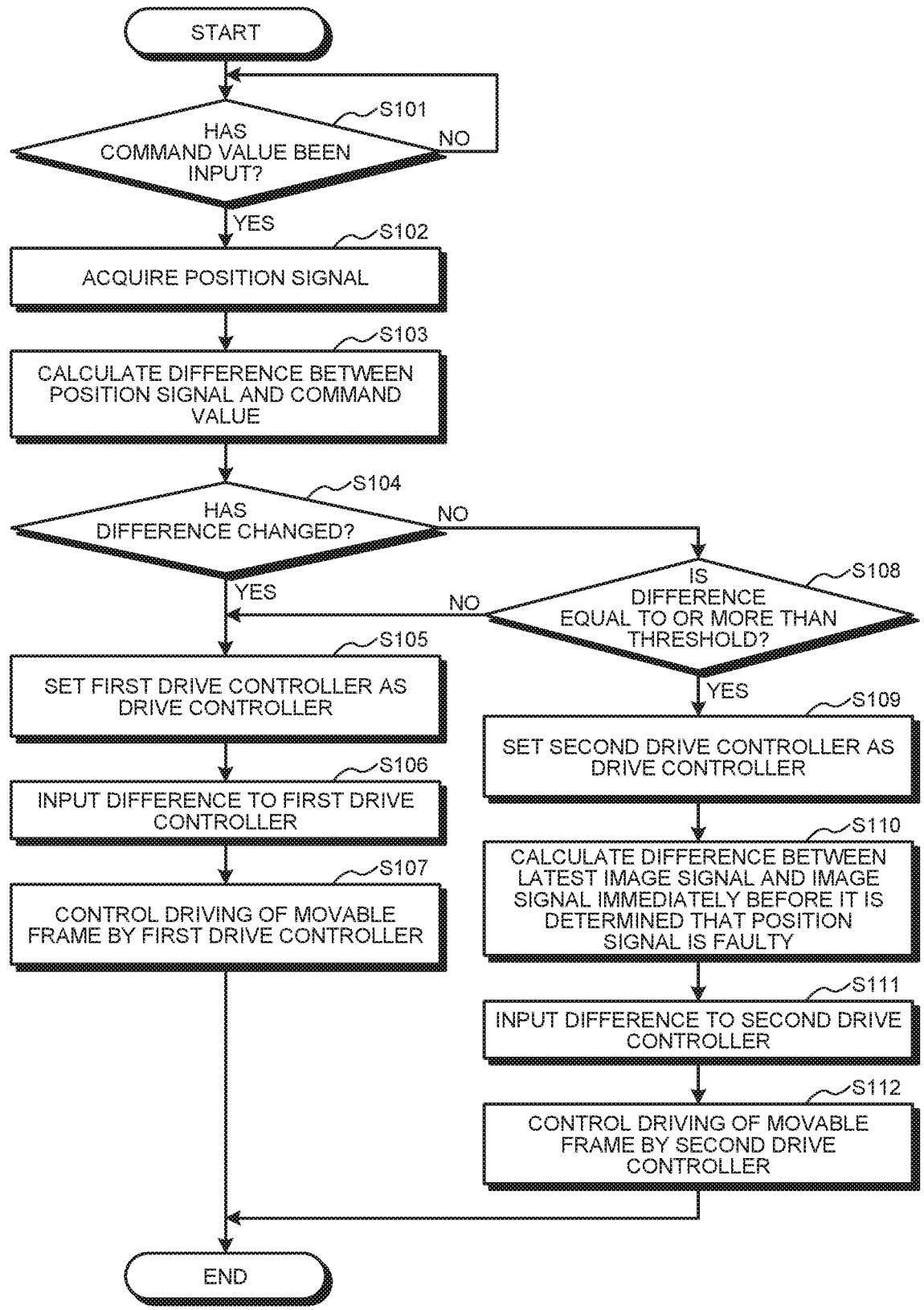
FIG. 5 is a flowchart that illustrates a process performed by the optical system according to the first embodiment.

Next, the drive control according to the first embodiment is explained with reference to FIG. 5. FIG. 5 is a flowchart that illustrates a process performed by the optical system according to the first embodiment. In explanation, during the drive control described below, if a command value is input and a position signal is normal, the control is performed until the movable frame 20 reaches the position (hereafter, referred to as the target position) that corresponds to the command value. Furthermore, with this flowchart, an explanation is given of a case where a command value is input via the input unit 31 for manual focusing; however, for automatic focusing, the control unit 38 generates command values.

First, the control unit 38 determines whether a command value has been input via the input unit 31 (Step S101). When it is determined that a command value has been input (Step S101: Yes), the control unit 38 proceeds to Step S102. Conversely, when it is determined that no command value has been input (Step S101: No), the control unit 38 repeatedly checks whether a command value has been input or terminates drive control.

At Step S102, the control unit 38 acquires a position signal from the position detecting unit 100. As described above, the position signal is obtained by converting the intensity of the magnetic field detected by the Hall element 14 into a voltage value.

After the position signal is acquired, the first-difference calculating unit 321 calculates the difference between the position signal (signal value) and the command value (Step S103). The first-difference calculating unit 321 inputs the calculated difference to the determining unit 322.

After the difference is input from the first-difference calculating unit 321, the determining unit 322 determines whether the difference has changed in terms of time (Step S104). For example, the determining unit 322 acquires the previous difference fetched from the buffer 37, e.g., the difference calculated immediately before the currently acquired difference, and compares the currently calculated difference with the previous difference so that it determines that the position signal is normal if there is a change in the difference and determines that there is a possibility that the position signal is faulty if the difference hardly changes. For example, the determining unit 322 determines whether a position signal is faulty on the basis of a difference between the above differences and the threshold stored in the drive-information storage unit 391. For example, the threshold is set in accordance with the minimum value of a difference between the differences that are assumed to be changed at least when the movable frame 20 is moved. The determining unit 322 inputs a determination result to the image processing unit 33. If a position signal is normal, the image processing unit 33 performs the above-described image data generation process, and the like.

When the determining unit 322 determines that there is a change in the difference (Step S104: Yes), the selector 34 sets the first drive controller 35 as a drive controller for controlling driving of the movable frame 20 (Step S105).

After the first drive controller 35 is set, the signal processing unit 32 inputs the difference calculated by the first-difference calculating unit 321 as a drive signal to the first drive controller 35 (Step S106).

After the difference is input as a drive signal, the first drive controller 35 controls driving of the movable frame 20 in accordance with the difference (Step S107). Specifically, the first drive controller 35 adjusts the amplitude or phase of the drive signal. The first drive controller 35 causes currents to flow into the coils 13A, 13B via the control unit 38 with the current value that corresponds to the adjusted drive signal, thereby controlling driving of the movable frame 20.

Conversely, at Step S104, when it is determined that there is no change in the difference (Step S104: No), the determining unit 322 determines whether the difference calculated at Step S103 is equal to or more than the threshold (Step S108). If the difference is less than the threshold (Step S108: No), the determining unit 322 determines that the position signal is normal and the movable frame 20 reaches the target position and then proceeds to Step S105. Conversely, if the difference is equal to or more than the threshold (Step S108: Yes), the determining unit 322 determines that the position signal is faulty and then proceeds to Step S109. The threshold at Step S108 is set on the basis of a difference that changes in terms of time during the control to retain the stop position of the movable frame 20 (fixed-position retaining control) (a difference in accordance with a movement of the movable frame 20 during the fixed-position retaining control). The determining unit 322 inputs a determination result to the image processing unit 33. Furthermore, if the determining unit 322 determines that a difference is equal to or more than the threshold (a position signal is faulty), it may be notified by using sound, light, images, or the like.

At Step S109, the selector 34 sets the second drive controller 36 as a drive controller for controlling drive of the movable frame 20 (Step S109).

If the judging unit 331 determines that the position signal is faulty on the basis of the determination result after the second drive controller 36 is set, the second-difference calculating unit 332 calculates a difference between contrast values in image data (Step S110). Specifically, the second-difference calculating unit 332 replaces the input command value with the contrast value in the image data immediately before it is determined that the position signal is faulty and calculates the difference between the contrast value in the currently acquired image signal and the contrast value with which the command value has been replaced (the contrast value when the position signal is normal). Then, the second-difference calculating unit 332 inputs the calculated difference to the second drive controller 36 (Step S111).

After the difference is input as a drive signal, the second drive controller 36 controls driving of the movable frame 20 on the basis of the difference (Step S112). Specifically, the second drive controller 36 adjusts the amplitude or phase of the drive signal. The second drive controller 36 causes currents to flow into the coils 13A, 13B via the control unit 38 with the current value that corresponds to the adjusted drive signal, thereby controlling driving of the movable frame 20. In this case, the drive control is a control to move the movable frame 20 to a position immediately before it is determined that the position signal is faulty.

The above-described drive control allows the movable frame 20 to move to a position where a certain degree of resolution is retained, i.e., a position before a failure occurs, even if a position signal is faulty and the movable frame 20 is out of control in the middle of a driving process. Furthermore, if the target position is reached (a difference becomes less than a threshold), the flow may be such that normal/abnormal determination of a position signal is terminated and only the normal position control of the movable frame 20 is conducted or the flow may be such that even if the target position is reached, normal/abnormal determination of a position signal is repeated and a position control is conducted.

According to the first embodiment described above, if the position signal detected by the position detecting unit 100 is normal, the movable frame 20 is controlled so as to be driven by using the position signal, and if the position signal is faulty, the movable frame 20 is controlled so as to be driven by using an imaging signal captured by the imaging device 3a, whereby if there is the single position detecting unit 100 and if the position of the movable lens 21 is not detected properly, it is possible to acquire images that retain such an image quality that treatment on the subject may be continued, and it is possible to prevent an increase in size.

Furthermore, according to the first embodiment, the detection magnet 25 is provided near the primary shaft 22 on a side surface in a direction perpendicular to the optical axis of the movable frame 20; therefore, even if the movable frame 20 fluctuates around the primary shaft 22 due to backlash between the primary shaft 22 and the shaft bearing 24, errors in position detection may be reduced.

Furthermore, according to the first embodiment, the movable frame 20 is formed by using a light metal or high-temperature resin so as to be lightweight as compared to the one formed by using metals other than a light metal, whereby the size of an actuator may be smaller and accordingly the size of the optical unit 2 may be smaller.

Furthermore, in explanation according to the first embodiment, the magnets 12A, 12B are provided in the fixed frame 10, and the coils 13A, 13B are provided in the movable frame 20; however, the coils 13A, 13B may be provided in the fixed frame 10, and the magnets 12A, 12B may be provided in the movable frame 20.

Furthermore, in explanation according to the first embodiment, the second drive controller 36 determines whether a focal point is set in accordance with a contrast value immediately before it is determined that a position signal is faulty and then controls driving of the movable frame 20; however, this is not a limitation, and a threshold may be provided and, until a contrast value exceeds the threshold, a feedback control is performed so that the movable frame 20 is controlled to be driven, a feedback control may be performed by using the maximum contrast value among contrast values within a predetermined time period instead of the previous contrast value, single scan auto focus (single scan AF) may be performed so that the movable frame 20 is controlled to be driven in accordance with a focus value, or the imaging device 3a may be provided with a phase-difference pixel and auto focus may be performed by using image-surface phase difference method so that the movable frame 20 is controlled to be driven in accordance with a focus value. For single scan AF, as there are no values with which a command value is replaced, the maximum value is detected from contrast values in image signals obtained within a certain number of steps (within a predetermined time period), and the command value is replaced with the maximum value. Furthermore, the size of a mask in an image may be detected so that the movable frame 20 is moved such that the size of the mask becomes a predetermined size.

In addition, the movable frame 20 may be controlled based on any value among luminance dispersion of pixel values (luminance values), the number of times of zero-crossing of a high-frequency component, the number of edges, and a difference in pixel values of adjacent pixels, or the movable frame 20 may be controlled by using the combination of these values including a contrast value.

For example, if luminance dispersion of pixel values (luminance values) is used, the image processing unit 33 determines whether a focal point is set by checking luminance dispersion of the pixel value of each pixel included in an imaging signal generated by the imaging device 3a. The contrast is clearer as luminance dispersion is larger, i.e., luminance values are more dispersed, and it is determined that a focal point is set when luminance dispersion is large.

Furthermore, if the number of times of zero-crossing of a high-frequency component is used, the image processing unit 33 extracts a signal value of a high-frequency component of the pixel value for each pixel included in an imaging signal generated by the imaging device 3a and conducts second derivative on signal values of high-frequency components of adjacent pixels. Values obtained by second derivative change from positive to negative or from negative to positive depending on a pixel location. This location (a combination of adjacent pixels) is called zero-cross, and it may be determined that a focal point is set as the number of times of zero-crossing is large. Therefore, if a threshold is provided for the number of times of zero-crossing, it may be determined whether a focal point is set.

Furthermore, if the number of edges is used, the image processing unit 33 first extracts a signal value of an edge component by filtering an image and calculates the number of edges by integrating signal values. An image includes more edge components as the number of edges is larger, and therefore it may be determined that a focal point is set. Thus, if a threshold is provided for the number of edges, it may be determined whether a focal point is set.

Moreover, if a difference between pixel values of adjacent pixels is used, the image processing unit 33 first calculates a difference between pixel values of adjacent pixels and integrates difference values to calculate the value of integral. As the value of integral is larger, a change between pixels is larger, and it may be determined that a focal point is set when a change is large. Thus, if a threshold is provided for the value of integral, it may be determined whether a focal point is set.

Modified Example of the First Embodiment

Figure 6:
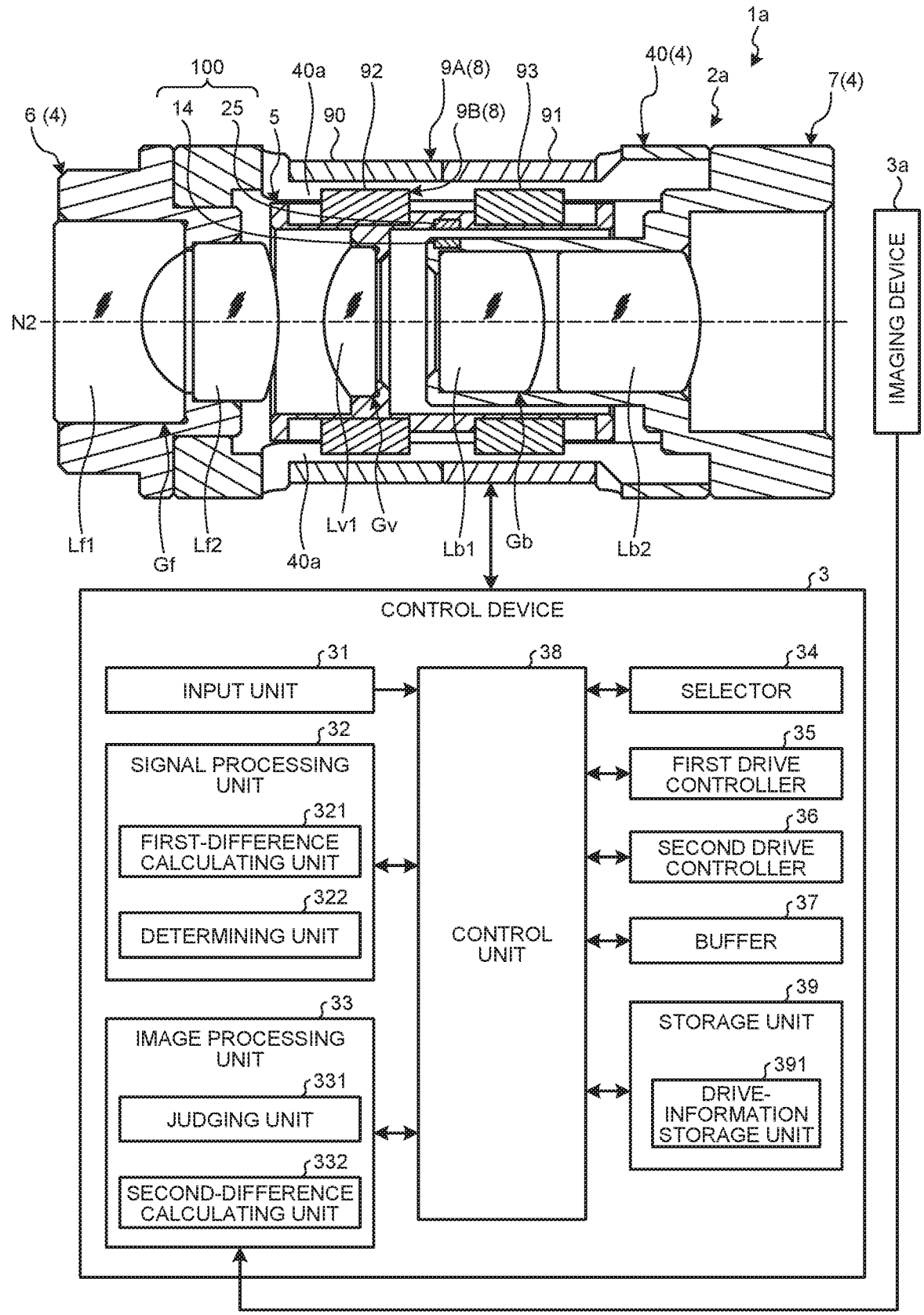
FIG. 6 is a schematic diagram that illustrates a schematic configuration of an optical system according to a modified example of the first embodiment.

In explanation according to the above-described first embodiment, the movable frame 20 is moved along the primary shaft 22; however, this is not a limitation. For example, a movable frame may be supported by a fixed frame and be moved while it slides on the inner circumference of the fixed frame. FIG. 6 is a schematic diagram that illustrates a schematic configuration of an optical system according to a modified example of the first embodiment, and it is a partial cross-sectional view whose cut plane is a plane passing through the optical axis. Furthermore, the same components as those described above are attached with the same reference numerals.

An optical system 1a according to this modified example includes an optical unit 2a that is capable of moving a lens in the direction of a light axis; the control device 3 that controls driving of each component including the optical unit 2a and controls input/output of information to and from each component; and the imaging device 3a that performs a photoelectric conversion process on light received via the optical unit 2a.

The optical unit 2a includes a fixed frame 4 (supporting frame), a movable frame 5 that is slidable on the fixed frame 4, and a voice coil motor 8 that generates a driving force for sliding the movable frame 5 on the fixed frame 4.

The fixed frame 4 includes a fixed-frame main body 40; a front frame portion 6 that is attached to the fixed-frame main body 40 at the side of an object and that supports an object-side fixed lens group Gf located closer to the object than a movable lens group Gv supported by the movable frame 5; and a rear frame portion 7 that is attached to the fixed-frame main body 40 at the side of imaging and that supports an imaging-side fixed lens group Gb located closer to imaging than the movable lens group Gv.

The fixed-frame main body 40 is a cylindrical member with a predetermined axis N2 as a center. The fixed-frame main body 40 is provided with a plurality of recess portions 40a passing through in a radial direction.

The front frame portion 6 is a cylindrical member. The front frame portion 6 supports the object-side fixed lens group Gf. The object-side fixed lens group Gf includes a first front lens Lf1 and a second front lens Lf2, and they are arranged in this order, starting from the object side. The front frame portion 6 holds the first front lens Lf1 and the second front lens Lf2 on its inner circumference.

The rear frame portion 7 is a cylindrical member. The rear frame portion 7 supports the imaging-side fixed lens group Gb. The imaging-side fixed lens group Gb includes a first rear lens Lb1 and a second rear lens Lb2. The rear frame portion 7 holds the first rear lens Lb1 and the second rear lens Lb2 on its inner circumference, starting from the object side in this order. Furthermore, the above-described Hall element 14 is provided on the outer circumference of the rear frame portion 7.

The movable frame 5 is a cylindrical member. The movable frame 5 supports the movable lens group Gv. Specifically, the movable frame 5 supports a first movable lens Lv1 included in the movable lens group Gv on its inner circumference. Furthermore, the above-described detection magnet 25 is provided on the inner circumference of the movable frame 5, and the Hall element 14 and the detection magnet 25 constitute the position detecting unit 100.

The movable frame 5 is inserted into the fixed-frame main body 40 such that part of its outer circumference is in contact with the inner circumference of the fixed-frame main body 40. Here, at least part of the imaging-side fixed lens group Gb is located in the inner side of the movable frame 5 in a radial direction, i.e., within a hollow space formed by the movable frame 5. According to this modified example, when the movable frame 5 is moved to the side closest to the object, at least part of the object-side fixed lens group Gf is located in the inner side of the movable frame 5 in a radial direction.

As illustrated in FIG. 6, the voice coil motor 8 includes a coil 9A provided in the fixed-frame main body 40 of the fixed frame 4; and a magnet 9B that is provided in the movable frame 5 such that it is opposed to the coil 9A.

The coil 9A is provided by winding two coils 90, 91 around the outer circumference of the fixed-frame main body 40 and arranging them along the direction of the axis N2. It is preferable that two adjacent coils along the direction of the axis N2 are connected in series; however, they may be connected in parallel.

A first magnet 92 and a second magnet 93 are provided in the movable frame 5 such that they enter the respective recess portions 40a of the fixed frame 4. Each of the first magnet 92 and the second magnet 93 includes for example four magnets provided along a circumferential direction. The group of the first magnet 92 and the group of the second magnet 93 are magnetized in a radial direction of the movable frame 5, and their magnetic poles are opposite to each other.

According to this modified example, it is preferable that the winding directions of the coils 90, 91 are reverse for the group of the first magnet 92 and the group of the second magnet 93. Alternatively, the winding directions of the coils 90, 91 may be set the same and the coils 90, 91 may be connected such that the electric-current directions are opposite. In this case, it is necessary that the direction of the current flowing through the coil 90 and the direction of the current flowing through the coil 91 be in opposite directions.

When a current flows into the coil 9A of the optical unit 2a, a force in the direction of the axis N2 occurs in the movable frame 5 due to an effect of the magnetic field in the magnet 9B, and the movable frame 5 is moved in the direction of the axis N2 relative to the fixed frame 4. For example, by controlling the current flowing in each of the coils 90, 91, the movable frame 5 may be moved relative to the fixed frame 4.

For the above-described drive control according to the first embodiment conducted by using the optical unit 2a that has the above-described configuration, if the position signal detected by the position detecting unit 100 is normal, drive control of the movable frame 5 is conducted by controlling the currents to the coils 90, 91 by using the position signal, and if the position signal is faulty, drive control of the movable frame 5 is conducted by controlling the currents to the coils 90, 91 by using imaging signals captured by the imaging device 3a. Thus, with the optical system 1a, an increase in size may be prevented and, even if the position of a movable lens is not properly detected, it is possible to retain such an image quality that treatment on a subject may be continued.

Furthermore, in explanation according to the first embodiment and the modified example, the Hall element is provided at the side of the fixed frame, and the detection magnet is provided at the side of the movable frame; however, the detection magnet may be provided at the side of the fixed frame and the Hall element at the side of the movable frame.

Furthermore, in explanation according to the first embodiment and the modified example, the Hall element is used as an example of the position detection sensor; however, positions may be detected by using an MR sensor.

Furthermore, according to the first embodiment and the modified example, positions may be detected by using a magnet of the voice coil motor without providing any detection magnet.

Furthermore, according to the first embodiment and the modified example described above, arrangement of the magnet of the voice coil motor and the coil may be opposite.

Furthermore, in explanation according to the first embodiment and the modified example described above, the Hall element sequentially converts the detected intensity of the magnetic field into a voltage value and outputs the voltage value based on the intensity of the magnetic field as a position signal to the control device; however, the intensity of the magnetic field may be output as a position signal to the control device. In this case, the intensity of the magnetic field is substituted for a voltage value and is each calculated.

Second Embodiment

Figure 7:
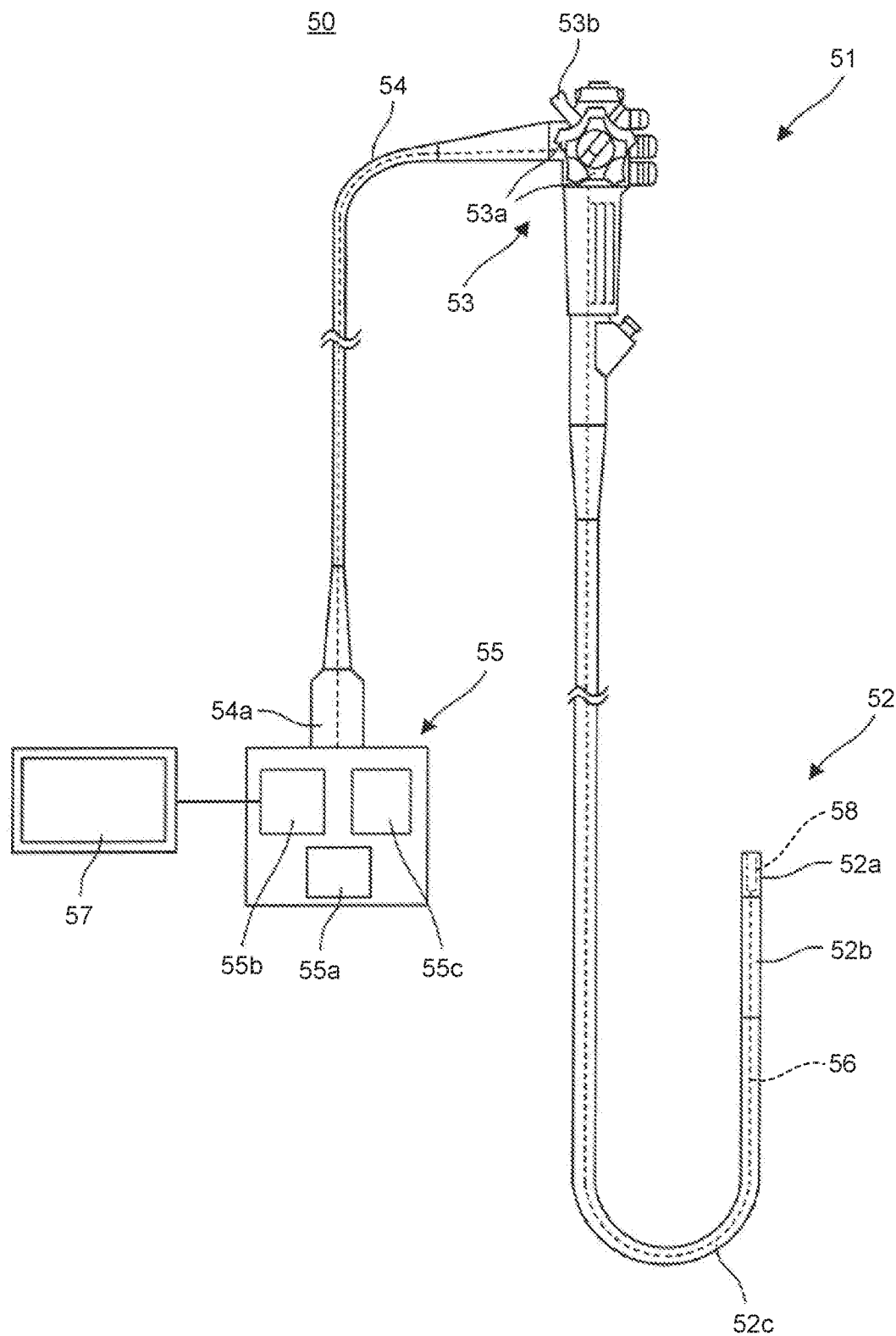
FIG. 7 is a diagram that illustrates a configuration of an endoscope system that includes an endoscope according to a second embodiment.

FIG. 7 is a diagram that illustrates a configuration of an endoscope system that includes an endoscope according to a second embodiment. An endoscope system 50 illustrated in FIG. 7 includes an endoscope 51, a control device 55, and a display device 57. The endoscope 51 includes any one of the optical systems 1, 1a according to the first embodiment or the modified example described above. The one that includes the optical system 1 (the optical unit 2) is explained as an example below.

The endoscope 51 may be introduced into a subject such as a human body, and it optically captures a predetermined observed region within the subject. Furthermore, the subject into which the endoscope 51 is introduced may be not only human bodies but also other living bodies, and it may be artificial material such as machines or buildings. In other words, the endoscope 51 may be endoscopes for medical use or endoscopes for industrial use.

The endoscope 51 includes an insertion unit 52 introduced into a subject; an operating unit 53 located at the proximal end of the insertion unit 52; and a universal code 54 that is a composite cable that extends from the operating unit 53.

The insertion unit 52 includes a distal end portion 52a provided at the distal end; a curved portion 52b that is provided at the proximal end of the distal end portion 52a and that may be curved; and a flexible tube section 52c that has flexibility and that is provided at the proximal end of the curved portion 52b and is connected to the distal end of the operating unit 53. At the distal end portion 52a, an imaging unit 58 is provided which collects light from the object and captures the object. The imaging unit 58 includes the optical unit 2 that collects light from the object; and the imaging device 3a that conducts photoelectric conversion on light collected by the optical unit 2 and outputs it. Furthermore, the endoscope 51 may be a rigid endoscope without providing the flexible tube section 52c in the insertion unit 52.

The operating unit 53 includes an angle operating unit 53a that performs operation for a curved state of the curved portion 52b; and an optical-unit operating unit 53b that designates operation of the above-described voice coil motors 30A, 30B and performs zoom operation or focusing operation in the optical unit 2. The angle operating unit 53a is shaped like a knob, and the optical-unit operating unit 53b is shaped like a lever; however, they may have a different shape such as a volume switch or a push switch.

The universal code 54 is a member that connects the operating unit 53 and the control device 55. The endoscope 51 is connected to the control device 55 via a connector 54a provided at the proximal end portion of the universal code 54.

A cable 56 such as a wire, electric line, or optical fiber, is inserted into the insertion unit 52, the operating unit 53, and the universal code 54.

The control device 55 includes a drive controller 55a that controls a curved state of the curved portion 52b; an image controller 55b that controls the imaging unit 58; and a light source controller 55c that controls an undepicted light source device. The control device 55 includes a processor such as a CPU (central processing unit), and it controls the entire endoscope system 50 in an integrated manner. The control device 55 includes the input unit 31, the signal processing unit 32, the selector 34, the buffer 37, and the storage unit 39, which are components of the above-described control device 3.

The drive controller 55a includes an actuator, and it is mechanically connected to the operating unit 53 and the curved portion 52b via a wire. The drive controller 55a controls a curved state of the curved portion 52b by moving the wire back and forth. Furthermore, the drive controller 55a includes the first drive controller 35 and the second drive controller 36, which are components of the above-described control device 3, and it performs a feedback control to move the movable frame 20 of the optical unit 2 to a desired position.

The image controller 55b is electrically connected to the imaging unit 58 and the operating unit 53 via the electric line. The image controller 55b conducts drive control on the voice coil motors 30A, 30B included in the imaging unit 58 and performs processing on images captured by the imaging unit 58. Images processed by the image controller 55b are displayed on the display device 57. Furthermore, the image controller 55b may include the image processing unit 33 so that the image processing unit 33 generates image data.

The light source controller 55c is optically connected to the light source and the operating unit 53 via an optical fiber.

The light source controller 55c controls the luminance of the light source emitted from the distal end portion 52a, and the like.

Furthermore, a configuration may be such that the operating unit 53 and the insertion unit 52 are separately formed and the insertion unit 52 is operated by remote control.

The endoscope system 50 with the above configuration includes the imaging unit 58 having the above-described optical unit 2, whereby zoom changes or focusing operation with a high accuracy and a reduction in size are possible. Furthermore, with the components of the control device 3, even if position signals from the position detecting unit 100 are faulty, it is possible to acquire images that retain such an image quality that treatment on the subject may be continued. Furthermore, if the optical unit 2 is applied to the endoscope system 50, it is preferable that heat resistant resin used for the movable frame 20, or the like, is resin that has a heat resistance property for, for example, over 140° C.

According to the present disclosure, there are advantages such that an increase in size may be prevented and, even if the position of a movable lens is not properly detected, it is possible to retain an image quality that treatment on the subject may be continued.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging device comprising:
   an optical lens configured to transmit light;
   a movable frame configured to support and move the optical lens in a predetermined direction;
   a supporting frame configured to support the movable frame;
   a voice coil motor including a magnet and a coil, the voice coil motor being configured to move the movable frame relative to the supporting frame in the predetermined direction:
   a position detecting sensor configured to detect information about a position of the movable frame relative to the supporting frame and generate a position signal;
   an imaging sensor configured to conduct photoelectric conversion on light passed through the optical lens to generate an imaging signal; and
   a controller comprising hardware, the controller being configured to:
      generate a drive signal including information about a movement distance and a moving direction of the movable frame relative to the supporting frame in accordance with the position signal generated by the position detecting sensor and determine whether the position signal is normal;
      generate an image signal based on the imaging signal;
      drive the movable frame with a first drive control by controlling a current flowing through the coil in accordance with the generated drive signal;
      drive the movable frame with a second drive control by controlling a current flowing through the coil in accordance with the generated image signal; and
      select a drive control that controls driving of the movable frame from the first drive control and the second drive control in accordance with a determination result of the signal processing unit;
   wherein the second drive control controls a current flowing through the coil so as to move the movable frame to a position where a representative signal value of the generated image signal becomes a predetermined value; and
   the predetermined value is a representative signal value of the image signal immediately before it is determined that the position signal is not normal.

2. The imaging device according to claim 1, wherein the controller is configured to select the first drive control when the controller determines that the position signal is normal and select the second drive control when the controller determines that the position signal is not normal.

3. The imaging device according to claim 1, wherein the controller is further configured to receive an input of a command signal to designate a move position of the movable frame, wherein
   the controller is configured to calculate a difference between a signal value of the position signal and a signal value of the command signal and determine whether the position signal is normal in accordance with the difference.

4. The imaging device according to claim 1, wherein the controller is further configured to generate a command value to designate a move position of the movable frame in accordance with the image signal, wherein
   the controller is configured to calculate a difference between a signal value of the position signal and the command value and determine whether the position signal is normal in accordance with the difference.

5. The imaging device according to claim 1, wherein the controller is configured to generate the image signal including at least one of a contrast value, a luminance value, and a phase difference.

6. The imaging device according to claim 1, wherein the second drive control conducts a feedback control on the movable frame in accordance with the generated image signal.

7. The imaging device according to claim 1, wherein the position detecting sensor comprises:
   a magnetic-field generator provided on one of the movable frame and the supporting frame and configured to generate a position-detection magnetic field; and
   a magnetic-field detector provided on another one of the movable frame and the supporting frame and configured to detect a magnetic field that is perpendicular to a moving direction of the movable frame.

8. An endoscope system comprising the imaging device according to claim 1, wherein the endoscope system is inserted into an inside of a subject to observe the inside of the subject.

9. An imaging device comprising:
   an optical lens configured to transmit light;
   a movable frame configured to support and move the optical lens in a predetermined direction;
   a supporting frame configured to support the movable frame;
   a voice coil motor including a magnet and a coil, the voice coil motor being configured to move the movable frame relative to the supporting frame in the predetermined direction;
   a position detecting sensor configured to detect information about a position of the movable frame relative to the supporting frame and generate a position signal;

an imaging sensor configured to conduct photoelectric conversion on light passed through the optical lens to generate an imaging signal; and a controller comprising hardware, the controller being configured to:

generate a drive signal including information about a movement distance and a moving direction of the movable frame relative to the supporting frame in accordance with the position signal generated by the position detecting sensor and determine whether the position signal is normal;

generate an image signal based on the imaging signal;

drive the movable frame with a first drive control by controlling a current flowing through the coil in accordance with the generated drive signal;

drive the movable frame with a second drive control by controlling a current flowing through the coil in accordance with the generated image signal; and select a drive control that controls driving of the movable frame from the first drive control and the second drive control in accordance with a determination result of the signal processing unit;

wherein the second drive control controls a current flowing through the coil so as to move the movable frame to a position where a representative signal value of the generated image signal becomes a predetermined value; and the predetermined value is a highest value among representative signal values of the image signals within a predetermined time period.

10. The imaging device according to claim 9, wherein the predetermined value is a value with which it is determined that a focal point is set by single scan auto focus.

11. The imaging device according to claim 9, wherein the controller is configured to select the first drive control when the controller determines that the position signal is normal and select the second drive control when the controller determines that the position signal is not normal.

12. The imaging device according to claim 9, wherein the controller is further configured to receive an input of a command signal to designate a move position of the movable frame, wherein the controller is configured to calculate a difference between a signal value of the position signal and a signal value of the command signal and determine whether the position signal is normal in accordance with the difference.

13. The imaging device according to claim 9, wherein the controller is further configured to generate a command value to designate a move position of the movable frame in accordance with the image signal, wherein the controller is configured to calculate a difference between a signal value of the position signal and the command value and determine whether the position signal is normal in accordance with the difference.

14. The imaging device according to claim 9, wherein the controller is configured to generate the image signal including at least one of a contrast value, a luminance value, and a phase difference.

15. The imaging device according to claim 9, wherein the second drive control conducts a feedback control on the movable frame in accordance with the generated image signal.

16. The imaging device according to claim 9, wherein the position detecting sensor comprises:

a magnetic-field generator provided on one of the movable frame and the supporting frame and configured to generate a position-detection magnetic field; and a magnetic-field detector provided on another one of the movable frame and the supporting frame and configured to detect a magnetic field that is perpendicular to a moving direction of the movable frame.

17. An endoscope system comprising the imaging device according to claim 9, wherein the endoscope system is inserted into an inside of a subject to observe the inside of the subject.

* * * * *